US012642450B2

(12) United States Patent (10) Patent No.: US 12,642,450 B2

Ouchi et al. (45) Date of Patent: Jun. 2, 2026

(54) NECK MOVEMENT MEASURING DEVICE

(71) Applicant: Murata Manufacturing Co., Ltd., Nagaokakyo (JP)

(72) Inventors: Tomoki Ouchi, Nagaokakyo (JP); Toru Yabe, Nagaokakyo (JP); Koji Tanaka, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 423 days.

(21) Appl. No.: 18/314,303

(22) Filed: May 9, 2023

(65) Prior Publication Data

US 2023/0404433 A1 Dec. 21, 2023

(30) Foreign Application Priority Data

May 23, 2022 (JP) ................................. 2022-084066

(51) Int. Cl.
*A61B 5/00* (2006.01)
*A61B 5/11* (2006.01)

(52) U.S. Cl.
CPC .............. *A61B 5/11* (2013.01); *A61B 5/4205* (2013.01); *A61B 5/6822* (2013.01); *A61B 2562/02* (2013.01)

(58) Field of Classification Search
CPC ....... A61B 5/11; A61B 5/6822; A61B 5/1107; A61B 5/228; A61B 5/6833; A61B 2562/02; A61B 2562/0261; A61B 2562/043; A61B 2/164
See application file for complete search history.

(56) References Cited

U.S. PATENT DOCUMENTS

| | | | |
|---|---|---|---|
| 8,941,392 B1 * | 1/2015 | Reese ...................... | G01B 7/22 |
| | | | 324/686 |
| 10,542,910 B2 | 1/2020 | Tanimura et al. | |
| 2017/0049361 A1 | 2/2017 | Tanimura et al. | |
| 2019/0069833 A1 * | 3/2019 | Tanaka ................. | A61B 5/08 |
| 2021/0191574 A1 * | 6/2021 | Sleeman ............. | G01L 1/142 |
| 2021/0310883 A1 | 10/2021 | Obata et al. | |
| 2023/0210496 A1 * | 7/2023 | Isla Garcia .......... | A61B 8/4477 |
| | | | 600/459 |

FOREIGN PATENT DOCUMENTS

| | | | |
|---|---|---|---|
| JP | 2000-272574 A | | 10/2000 |
| JP | 2010-122083 A | | 6/2010 |
| JP | 2015-208634 A | | 11/2015 |
| JP | 2017-056053 A | | 3/2017 |
| JP | 2018-153648 A | | 10/2018 |
| JP | 2019-017673 A | | 2/2019 |
| JP | 2020103429 A | * | 7/2020 |
| JP | 2022007091 A | | 1/2022 |
| WO | 2018/182043 A1 | | 10/2018 |
| WO | 2020/166122 A1 | | 8/2020 |

* cited by examiner

*Primary Examiner* — Robert L Nasser
(74) *Attorney, Agent, or Firm* — ArentFox Schiff LLP

(57) ABSTRACT

A neck movement measuring device is provided that includes displacement sensors and a controller. The displacement sensors are formed as sheets attachable to the neck skin of a subject and measure the deformation amount. The controller receives measured values of the displacement sensors and sets a reference value based on measured values of the displacement sensor. In addition, the controller outputs the displacement amount relative to the reference value as a measurement result.

13 Claims, 3 Drawing Sheets

NECK MOVEMENT MEASURING DEVICE

CROSS REFERENCE TO RELATED APPLICATIONS

This application claims priority to Japanese Patent Application No. 2022-084066, filed May 23, 2022, the entire contents of each of which are hereby incorporated by reference in their entirety.

TECHNICAL FIELD

The present disclosure relates to a neck movement measuring device.

BACKGROUND

A swallowing movement measuring device is described in Japanese Patent Application Publication No. 2022-7091 (hereinafter "Patent Document 1") and includes a handle, a fixation portion, and a capacitive sensor. The handle is shaped as a rod so that a person, such as a subject, can hold the handle. The fixation portion is joined to an end portion of the handle in a rotatable manner. The capacitive sensor is joined to the fixation portion. Moreover, the capacitive sensor is a sheet-like capacitive sensor that detects movements of the thyroid cartilage of a subject by sensing changes in electrostatic capacity.

A user using the swallowing movement measuring device described in Patent Document 1 holds the capacitive sensor to the neck of a subject to measure swallowing movement of the subject. However, the surface shape of neck slightly varies among subjects, which can adversely affect the accuracy of measurement results of swallowing movement.

Although the above description uses a swallowing movement measuring device as an example, the same problem can occur with any device for measuring neck movement, such as throat movement or neck movement, using a sensor held on the outer surface of the neck.

SUMMARY OF THE INVENTION

In view of the foregoing problems, the present invention provides a neck movement measuring device that includes a displacement sensor attachable to the neck of a subject and a controller configured to output a measured value of the displacement sensor. The controller is configured to set a reference value based on a measured value of the displacement sensor and output a displacement amount relative to the reference value as a measurement result of the displacement sensor.

With this configuration, the reference value is set based on a measured value of the displacement sensor. As a result, a reference value corresponding to the surface shape of the subject is set, and based on the displacement amount relative to the reference value, the subject's neck movement is detected. This configuration reduces the effects of variations in the attachment manner of the displacement sensor on the detection of neck movement.

DETAILED DESCRIPTION OF EMBODIMENTS

Hereinafter, an exemplary embodiment of a neck movement measuring device will be described. For ease of understanding, constituent elements are illustrated in an enlarged manner in some of the drawings. In some of the drawings, the measurement ratio of constituent elements is different from the actual measurement ratio or the measurement ratio in other drawings.

Overall Structure

Figure 1:
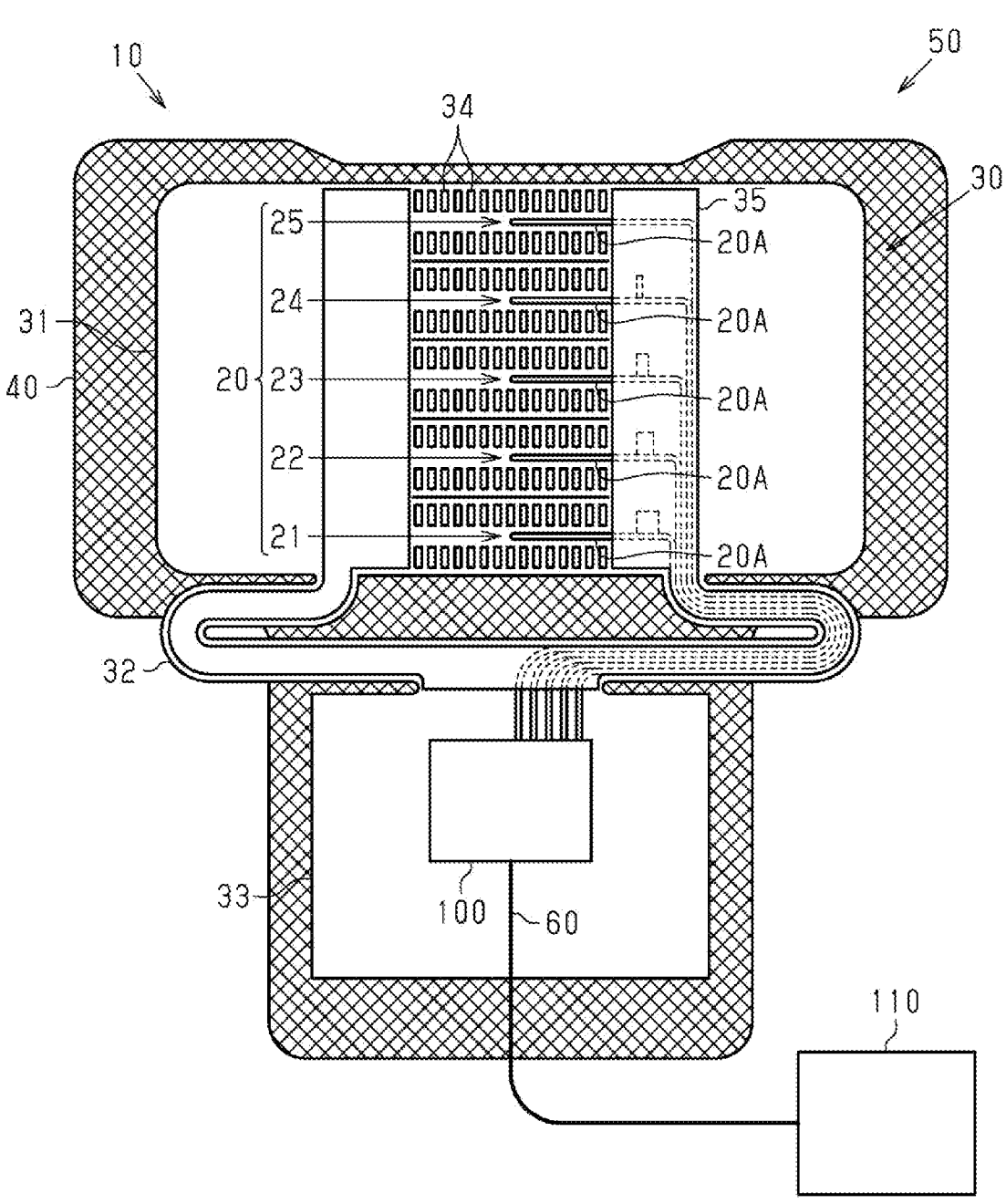
FIG. 1 is a general view of a neck movement measuring device according to an exemplary aspect.

As illustrated in FIG. 1, a neck movement measuring device 10 includes a body 50 and a controller 100. As illustrated in FIG. 1, the body 50 includes a sensor sheet 30, five displacement sensors 20, and a fixation member 40.

According to the exemplary aspect of FIG. 1, the sensor sheet 30 is made of a stretchy synthetic resin. It is preferable that the sensor sheet 30 contain, for example, a material with low elasticity, such as a polyurethane, acrylic, or silicone resin. The sensor sheet 30 is shaped as a sheet.

As further shown, the sensor sheet 30 includes a detector 31, a connector 32, and a terminal unit 33. The detector 31 is substantially rectangular in a plan view. Moreover, the connector 32 is shaped as a strip with a first end and a second end of the connector 32 being connected to a long side of the edges of the detector 31. This means that the connector 32 is extended to form almost a loop. In addition, the terminal unit 33 can be substantially rectangular in a plan view. The terminal unit 33 is positioned opposite to the detector 31 with respect to the connector 32. The terminal unit 33 is connected to the connector 32. In other words, the detector 31 and the terminal unit 33 are coupled by the connector 32.

The displacement sensors 20 are made of an electrical conductor and can be made of a material with resistance that greatly changes with expansion and contraction. The material of the displacement sensors 20 is, for example, a mixture of a metal in powder form such as silver or copper and an elastomeric resin such as a silicone. The displacement sensors 20 are shaped as lines.

Moreover, the displacement sensors 20 are disposed on the sensor sheet 30. A first end of each displacement sensor 20 is disposed on the terminal unit 33. The displacement sensors 20 are extended from the terminal unit 33 via the connector 32 to the detector 31. The displacement sensors 20 are extended back from the detector 31 via the connector 32 to the terminal unit 33.

Here, an axis along a long side of the detector 31 is designated as a long axis. A portion of the displacement sensor 20 is a sensing portion 20A elongated parallel to the long axis. The five displacement sensors 20 each include the sensing portion 20A. The sensing portions 20A of the displacement sensors 20 are arranged parallel to each other. This means that the sensing portions 20A of the five displacement sensors 20 are arranged in the direction from the detector 31 to the terminal unit 33. Thus, the sensing portions 20A of the displacement sensors 20 can be positioned at regular intervals.

In the exemplary aspect, the resistance of the displacement sensor 20 changes as the length of the corresponding sensing portion 20A in the direction along the long axis at the detector 31 changes. By sensing a change in the resistance, the displacement sensors 20 measures the amount of deformation of an object under measurement. This means that the displacement sensors 20 are deformation sensors. For example, when no force is applied from outside, the displacement sensors 20 are straight. By force applied from outside, one or more of the displacement sensors 20 is bent. The displacement sensor 20 senses the degree of this bend as the amount of deformation. The displacement sensor 20 transmits a signal corresponding to the amount of deformation.

The sensor sheet 30 described above has a plurality of slits 34 that are positioned at the detector 31. The slits 34 are elongated perpendicular to the long axis. The slits 34 are arranged on both sides with respect to the sensing portions 20A of the displacement sensors in the direction perpendicular to the long axis. The configuration of the slits 34 facilitate deformation of the detector 31.

Moreover, the body 50 includes a support sheet 35. The support sheet 35 is stuck to the detector 31 and the connector 32, with the displacement sensors 20 between the support sheet 35, and the detector 31 and the connector 32. This means that, of the support sheet 35, the surface facing the detector 31 and the connector 32 has an adhesive. The support sheet 35 covers a portion of each of the five displacement sensors 20, excluding the sensing portion 20A. As such, the support sheet 35 fixes the displacement sensors 20 on the sensor sheet 30 in the manner in which deformation measurement by the displacement sensors 20 is not obstructed.

The fixation member 40 is shaped as a sheet. The tensile load of the fixation member 40 is greater than the tensile load of the sensor sheet 30. In exemplary aspects, the material of the fixation member 40 can be, for example, urethane rubber, silicon rubber, nitrile rubber sponge, chloroprene rubber sponge, or ethylene rubber sponge. The fixation member 40 is positioned opposite to the displacement sensors 20 and the support sheet 35 with respect to the sensor sheet 30. The fixation member 40 is stuck to the sensor sheet 30. The fixation member 40 is larger in size than the detector 31 and the terminal unit 33 of the sensor sheet 30 by some degree. The fixation member 40 covers the almost entire portion of the sensor sheet 30. Of the fixation member 40, the surface opposite to the side stuck to the sensor sheet 30 has an adhesive. The body 50 is attachable to a subject using the fixation member 40. In general, the terms "subject" and "user" are used interchangeably in this disclosure to refer, for example, to a person wearing and using the neck movement measuring device 10.

Figure 2:
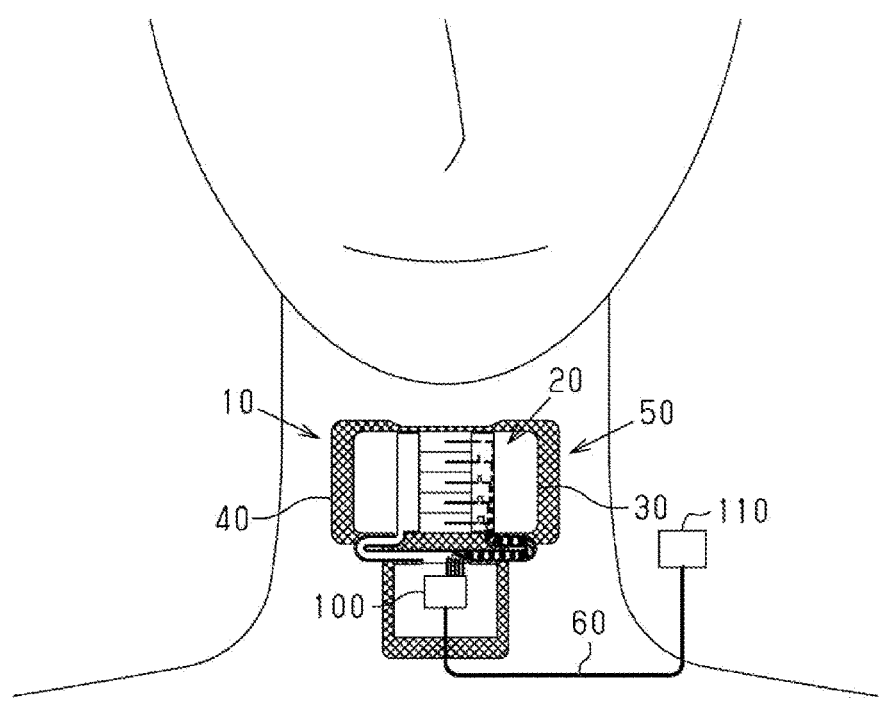
FIG. 2 illustrates the neck movement measuring device in the state in which a body of the neck movement measuring device is attached to a subject according to an exemplary aspect.

As illustrated in FIG. 2, the body 50 is attached to, for example, the neck skin near the larynx of a subject. The body 50 is attached to a subject such that the fixation member 40 is in contact with the skin of the subject. In the state in which the body 50 is attached to the subject, the displacement sensor 20 closest to the lower jaw of the five displacement sensors on the detector 31 is positioned on the side close to the lower jaw of the thyroid cartilage. The displacement sensor 20 farthest from the lower jaw of the five displacement sensors 20 is positioned on the side away from the lower jaw of the thyroid cartilage.

In the following description, when it is necessary to identify the five displacement sensors 20, as illustrated in FIG. 1, of the five displacement sensors 20 on the detector 31, the displacement sensor 20 farthest from the lower jaw is referred to as a first displacement sensor 21; the other displacement sensors 20 are referred to, in order of closeness to the first displacement sensor 21, as a second displacement sensor 22, a third displacement sensor 23, a fourth displacement sensor 24, and a fifth displacement sensor 25.

Controller

As illustrated in FIG. 1, the controller 100 is connected to the terminal unit 33 at the sensor sheet 30. The controller 100 is coupled to the displacement sensors 20 and configured to receive signals transmitted by the displacement sensors 20. In other words, the controller 100 receives measured values about the amount of deformation from the displacement sensors 20. The controller 100 is configured to be coupled to an external device 110 using, for example, a cable 60. The controller 100 outputs measurement results obtained by the displacement sensors 20 and related information to the external device 110.

The controller 100 is operable to set a reference value B0. As an operation prior to setting the reference value B0, the controller 100 firstly receives measured values from the displacement sensors 20. The controller 100 then determines whether the individual measured values from the displacement sensors 20 indicate a deformation greater than or equal to a predetermined particular value, which can be a threshold value set in advance of operation. Here, when a measured value from the displacement sensor 20 is close to the given value described above, the displacement sensor 20 is planar or in a similar shape. As a result, when a measured value from the displacement sensor 20 is close to the given value, it is assumed that the displacement sensor 20 is in the state in which little deformation is made before the displacement sensor 20 is attached to a subject. Hence, when measured values from the displacement sensors 20 are not in a range of, for example, plus or minus 5% of the given (e.g., preset or predetermined) value described above, the controller 100 determines that the measured values indicate a deformation greater than or equal to the predetermined particular value.

Next, when all the measured values from the five displacement sensors 20 indicate a deformation greater than or equal to the particular value, the controller 100 starts setting of the reference value B0. The controller 100 designates a measured value measured by each displacement sensor 20 for the first time since the controller 100 starts setting of the reference value B0 as a first measured value A0.

In the process of setting the reference value B0, the controller 100 sets measured values measured by the displacement sensors 20 in a particular period as the reference value B0. Specifically, when the difference between the greatest and smallest values of measured values measured by each displacement sensor 20 in a predetermined specific period is a predetermined specific value or smaller, the controller 100 sets as the reference value B0 one value selected from the measured values measured by the displacement sensor 20 in the specific period. Thus, the "particular period" is a period for which measured values measured by the displacement sensors 20 are the specific value or smaller. This is, for example, the state in which a subject with the sensor attached keeps still without swallowing movement for the specific period (e.g., a specific time period).

In the present embodiment, the specific period described above is, for example, several seconds. In the present embodiment, a value that allows electrical noises and variations in measured values due to subject's unintentional subtle movement is designated as the specific value. For example, when the first measured value A0 is deemed as 100%, plus or minus 0.5% of the first measured value A0 is predetermined as the specific value. In the present embodiment, the reference value B0 is the average value of measured values measured in the specific period. The reference value B0 is set for each displacement sensor 20.

In the neck movement measuring device 10, whether the reference value B0 has been set is determined in the following manner. Firstly, the five displacement sensors 20 are brought into a planar state. The controller 100 starts setting of the reference value B0 and sets the reference value B0. Subsequently, the displacement sensors 20 are changed in position to obtain measured values. Next, after a power supply of the controller 100 is reset, the five displacement sensors 20 are bent. The controller 100 then starts setting of the reference value B0 and sets the reference value B0. Subsequently, the displacement sensors 20 are bent to the same extent as in the above operation to obtain measured values. When the measured values in this operation are almost the same as the measured values in the previous operation, it is determined that the reference value B0 has been set.

Figure 3:
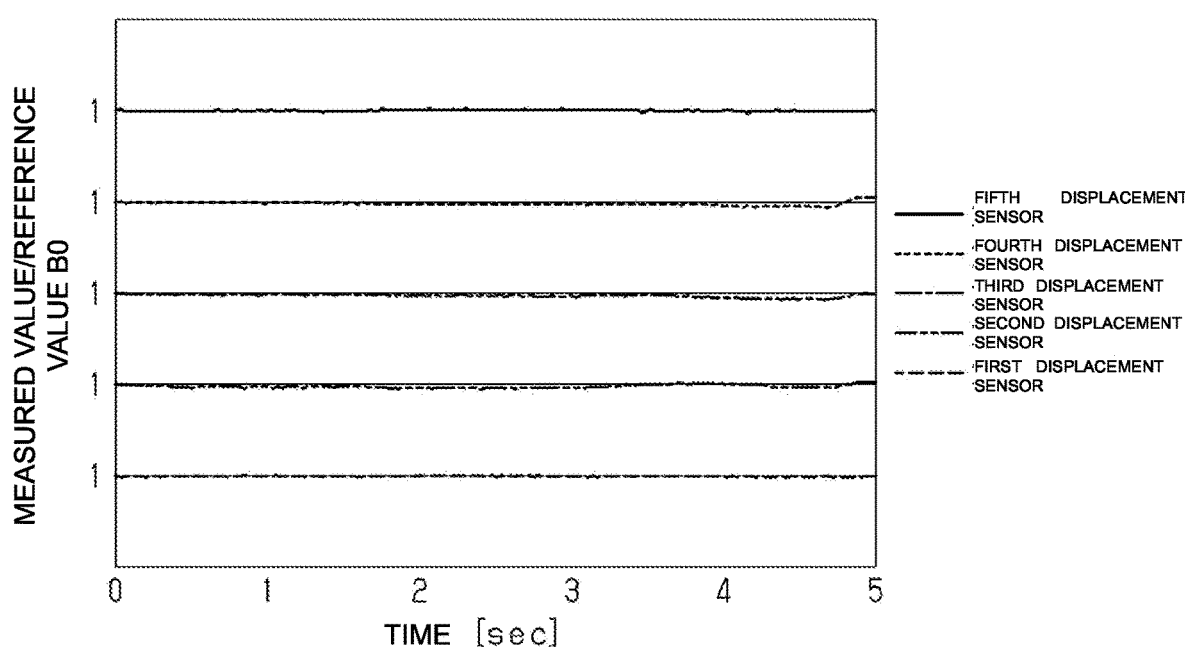
FIG. 3 illustrates plots of sensed values of displacement sensors after reference values are set in the neck movement measuring device according to an exemplary aspect.

In the exemplary aspect, the controller 100 is configured to perform a measurement operation. In the measurement operation, the controller 100 outputs the displacement amount relative to the reference value B0 as a measurement result by the displacement sensor 20. Specifically, as illustrated in FIG. 3, the controller 100 calculates a sensed value B1 that is a value indicating the displacement amount of the displacement sensor 20 relative to the reference value B0. In the present embodiment, the sensed value B1 is a value obtained by dividing a measured value by the reference value B0. As a result, as illustrated in FIG. 3, while the measured value is almost equal to the reference value B0, the sensed value B1 remains close to "1". As the difference between the measured value and the reference value B0 increases, the difference of the sensed value B1 deviates from "1".

The controller 100 outputs the sensed value B1 to the external device 110. The sensed value B1 is displayed on a display included in the external device 110. Based on the sensed value B1, the controller 100 can be configured to detect masticatory movement, swallowing movement, or neck flexion movement as subject's neck movement in the measurement operation. Details of the detection of neck movement by the controller 100 will be described below.

In operation, the controller 100 is further configured to output an identification signal corresponding to the detected movement, which is masticatory movement, swallowing movement, or neck flexion movement, to the external device 110. An image and information in text indicating masticatory movement, swallowing movement, or neck flexion movement are displayed on a display included in a computer of the external device 110. In the description of the embodiment, measured values measure by the displacement sensors 20 are outputted to the external device 110, but this is not to be interpreted as limiting. For example, the neck movement measuring device 10 may include a display and a computer, and measured values may be outputted to the display and computer.

Neck Movement

Moreover, the controller 100 is configured to determine masticatory movement, swallowing movement, or neck flexion movement based on the sensed value B1.

Masticatory movement is a movement of moving up or down the lower jaw. Swallowing movement is a movement of making an object in the oral cavity go down into the esophagus. Neck flexion movement is a movement in which the subject moves the neck forwards, backwards, leftwards, or rightwards.

In an exemplary aspect, the controller 100 is configured to determine whether the sensed value B1 of each displacement sensor 20 is greater than or equal to a predetermined first upper limit XU1, or smaller than or equal to a predetermined first lower limit XD1. The first upper limit XU1 and the first lower limit XD1 are determined by conducting a test in the following manner. Firstly, the displacement sensors 20 are attached to a subject for actual use. After the reference value B0 is set as described above, the measurement operation described above is performed while the subject performs masticatory movement. The maximum and minimum values of the sensed value B1 sensed in this operation by the displacement sensors 20 are detected. A value slightly smaller than the maximum value detected as described above is designated as the first upper limit XU1. Similarly, a value slightly greater than the minimum value detected as described above is designated as the first lower limit XD1. For example, the first upper limit XU1 is "1.01", and the first lower limit XD1 is "0.99".

The sensed value B1 represents the difference between a measured value and the reference value B0. When the sensed value B1 is greater than or equal to "1.01" that is the first upper limit XU1, this means that the absolute value of the difference between the measured value and the reference value B0 is greater than or equal to 1% of the reference value B0. As a result, in this embodiment, a first threshold X1 is a value equal to 1% of the reference value B0. The same holds for the case in which the sensed value B1 is smaller than or equal to the first lower limit XD1.

The controller 100 also determines whether the sensed value B1 of each displacement sensor 20 is greater than or equal to a predetermined second upper limit XU2, or smaller than or equal to a predetermined second lower limit XD2. The second upper limit XU2 and the second lower limit XD2 are determined by conducting a test in the following manner. Firstly, the displacement sensors 20 are attached to the subject for actual use. After the reference value B0 is set as described above, the measurement operation described above is performed during swallowing movement of the subject. The maximum and minimum values of the sensed value B1 sensed in this operation by the displacement sensors 20 are detected. A value slightly smaller than the maximum value detected as described above is designated as the second upper limit XU2. Similarly, a value slightly greater than the minimum value detected as described above is designated as the second lower limit XD2. For example, the second upper limit XU2 is "1.03", and the second lower limit XD2 is "0.97".

When the sensed value B1 is greater than or equal to "1.03" that is the second upper limit XU2, this means that the absolute value of the difference between the measured value and the reference value B0 is greater than or equal to 3% of the reference value B0. As a result, in this embodiment, a second threshold X2 is a value equal to 3% of the reference value B0. The same holds for the case in which the sensed value B1 is smaller than or equal to the second lower limit XD2.

Similarly, the controller 100 also determines whether the sensed value B1 of each displacement sensor 20 is greater than or equal to a predetermined third upper limit XU3, or smaller than or equal to a predetermined third lower limit XD3. The third upper limit XU3 and the third lower limit XD3 are determined by conducting a test in the following manner. Firstly, the displacement sensors 20 are attached to the subject for actual use. After the reference value B0 is set as described above, the measurement operation described above is performed during neck flexion movement of the subject. The maximum and minimum values of the sensed value B1 sensed in this operation by the displacement sensors 20 are detected. A value slightly smaller than the maximum value detected as described above is designated as the third upper limit XU3. Similarly, a value slightly greater than the minimum value detected as described above is designated as the third lower limit XD3. For example, the third upper limit XU3 is "1.07", and the third lower limit XD3 is "0.93".

When the sensed value B1 is greater than or equal to "1.07" that is the third upper limit XU3, this means that the absolute value of the difference between the measured value and the reference value B0 is greater than or equal to 7% of the reference value B0. As a result, in this embodiment, a third threshold X3 is a value equal to 7% of the reference value B0. The same holds for the case in which the sensed value B1 is smaller than or equal to the third lower limit XD3.

When the sensed value B1 sensed by each displacement sensor 20 is greater than or equal to the first threshold X1 and smaller than the second threshold X2, the controller 100 detects masticatory movement of the subject. Specifically, when the sensed value B1 of one or more of the five displacement sensors 20 is greater than or equal to the first upper limit XU1 and smaller than the second upper limit XU2, the controller 100 detects masticatory movement of the subject. Moreover, when the sensed value B1 of one or more of the five displacement sensors 20 is smaller than or equal to the first lower limit XD1 and greater than the second lower limit XD2, the controller 100 detects masticatory movement of the subject. When masticatory movement of the subject is detected in either manner, the controller 100 transmits an identification signal representing masticatory movement of the user.

When the sensed value B1 sensed by each displacement sensor 20 is greater than or equal to the second threshold X2 and smaller than the third threshold X3, the controller 100 detects swallowing movement of the subject. Specifically, when the sensed value B1 of one or more of the five displacement sensors 20 is greater than or equal to the second upper limit XU2 and smaller than the third upper limit XU3, the controller 100 detects swallowing movement of the subject. Moreover, When the sensed value B1 of one or more of the five displacement sensors 20 is smaller than or equal to the second lower limit XD2 and greater than the third lower limit XD3, the controller 100 detects swallowing movement of the subject. When swallowing movement of the subject is detected in either manner, the controller 100 transmits an identification signal representing swallowing movement of the user.

When the sensed value B1 sensed by each displacement sensor 20 is greater than or equal to the third threshold X3, the controller 100 detects neck flexion movement of the subject. Specifically, when the sensed value B1 of one or more of the five displacement sensors 20 is greater than or equal to the third upper limit XU3, the controller 100 detects neck flexion movement of the subject. Moreover, when the sensed value B1 of one or more of the five displacement sensors 20 is smaller than or equal to the third lower limit XD3, the controller 100 detects neck flexion movement of the subject. When neck flexion movement of the subject is detected in either manner, the controller 100 transmits an identification signal representing neck flexion movement of the user.

Technical Effects of the Exemplary Embodiment

Figure 4:
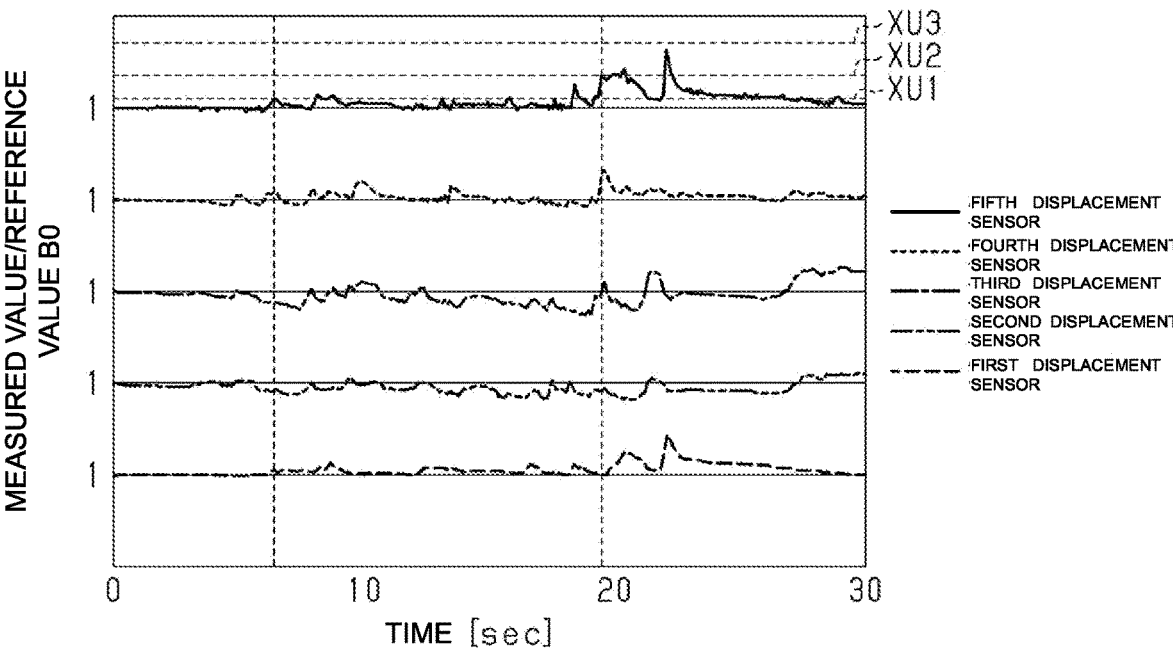
FIG. 4 illustrates plots of sensed values of displacement sensors after reference values are set in the neck movement measuring device according to an exemplary aspect.

After setting the reference value B0, the controller 100 performs the measurement operation. It is assumed that as illustrated in FIG. 4, the subject performs masticatory movement between about 7 seconds and about 19 seconds since the start of measurement operation. In this case, in the example illustrated in FIG. 4, at about 7 seconds since the start of measurement operation, the sensed value B1 of the fifth displacement sensor 25 is greater than or equal to the first upper limit XU1 and smaller than the second upper limit XU2. Accordingly, the controller 100 detects masticatory movement of the subject at about 7 seconds. The controller 100 transmits an identification signal representing masticatory movement. While the sensed value B1 of any of the five displacement sensors 20 is greater than or equal to the first upper limit XU1 and smaller than the second upper limit XU2, the controller 100 continuously detects masticatory movement. Similarly, while the sensed value B1 of any of the five displacement sensors 20 is smaller than or equal to the first lower limit XD1 and greater than the second lower limit XD2, the controller 100 continuously detects masticatory movement of the subject.

It is assumed that after masticatory movement, the subject performs swallowing movement at about 19 seconds since the start of measurement operation. In this case, in the example illustrated in FIG. 4, at about 19 seconds since the start of measurement, the sensed value B1 of the fifth displacement sensor 25 is greater than or equal to the second upper limit XU2 and smaller than the third upper limit XU3. Accordingly, the controller 100 detects swallowing movement of the subject at about 19 seconds. The controller 100 transmits an identification signal representing swallowing movement. Afterwards, every time swallowing movement is performed, the sensed value B1 of any of the displacement sensors 20 is greater than or equal to the second upper limit XU2 and smaller than the third upper limit XU3; otherwise, the sensed value B1 of the displacement sensor 20 becomes smaller than or equal to the second lower limit XD2 and greater than the third lower limit XD3.

Figure 5:
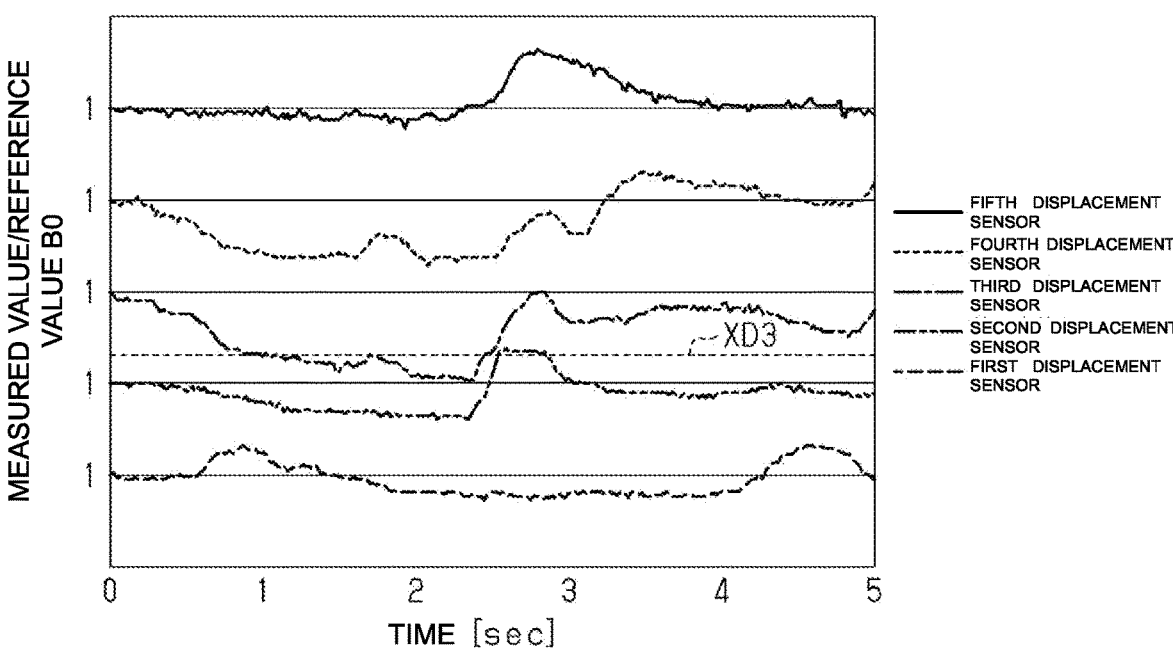
FIG. 5 illustrates plots of sensed values of displacement sensors after reference values are set in the neck movement measuring device according to an exemplary aspect.

It is also assumed that as illustrated in FIG. 5, the subject performs neck flexion movement between about 1 seconds and about 3 seconds since the start of measurement operation. In this case, in the example illustrated in FIG. 5, at about 1 second since the start of measurement operation, for example, the sensed value B1 of the third displacement sensor 23 is smaller than or equal to the third lower limit XD3. Accordingly, the controller 100 detects neck flexion movement of the subject at about 1 second and then transmits an identification signal representing neck flexion movement of the user. Afterwards, every time neck flexion movement is performed, the sensed value B1 of any of the displacement sensors becomes greater than or equal to the third upper limit XU3. Otherwise, the sensed value B1 of any of the displacement sensors 20 is smaller than or equal to the third lower limit XD3.

According to the embodiment described above, a measured value in the particular period is set as the reference value B0. As a result, although the displacement sensors 20 can be attached in a variety of manners, the reference value B0 is set based on the variation. Further, neck movement is detected based on the difference between the reference value B0 and a measured value. As such, the effects of variations in the attachment manner of the displacement sensors 20 on the detection of neck movement can be reduced.

According to the embodiment described above, when the difference between the greatest and smallest values of measured values measured by each displacement sensor 20 in a predetermined specific period is a predetermined specific value or smaller, the controller 100 sets the reference value B0. This means that the reference value B0 is set at a measured value measured in the state in which variations of measured values of the displacement sensors 20 are relatively small, for example the state in which the displacement sensors 20 are stably attached. As a result, the detection result of neck movement is more reliable.

In the embodiment described above, when all the measured values from the five displacement sensors 20 indicate a deformation greater than or equal to the predetermined particular value, the controller 100 starts setting of the reference value B0. This means that the reference value B0 is not set in the state in which there is a probability that neck movement is unmeasurable, for example before the displacement sensors 20 are attached to the subject. As such, according to the embodiment described above, the possibility that the reference value B0 can be set in an incorrect state can be reduced.

According to the embodiment described above, the controller 100 detects in the measurement operation masticatory movement, swallowing movement, or neck flexion movement as neck movement, which can generally be considered first, second and third next movements. This means that with the neck movement measuring device 10 of the embodiment, the subject's neck motions can be analyzed by classifying the motions under a plurality of kinds of movement.

In the embodiment described above, when the sensed value B1 is greater than or equal to the first threshold X1 and smaller than the second threshold X2, masticatory movement is detected as neck movement of the user. In masticatory movement, the neck motion is smaller than swallowing movement and neck flexion movement. According to the embodiment described above, masticatory movement is detected based on actual neck movement.

In the embodiment described above, when the sensed value B1 is greater than or equal to the second threshold X2 and smaller than the third threshold X3, swallowing movement is detected as neck movement of the user. In swallowing movement, the neck motion is larger than masticatory movement, but smaller than neck flexion movement. According to the embodiment described above, swallowing movement is detected based on actual neck movement.

In the embodiment described above, when the sensed value B1 is greater than or equal to the third threshold X3, neck flexion movement is detected as neck movement of the user. In neck flexion movement, the neck motion is larger than masticatory movement and swallowing movement. According to the embodiment described above, neck flexion movement is detected based on actual neck movement.

Modifications of the Exemplary Embodiment

The present embodiment is implementable as the following modifications. The present embodiment and the following modifications may be combined in any combination when there is no technical contradiction.

In the embodiment described above, the structure of the body 50 is not limited to the example in the embodiment described above. For example, the body 50 may include a plurality of sensor sheets 30, and the displacement sensors 20 are stuck to the respective sensor sheets 30.

In the embodiment described above, when at least one displacement sensor 20 is included, any number of displacement sensors 20 may be included. The number of displacement sensors 20 may be one to four, or six or greater in alternative aspects. In the embodiment described above, when the displacement sensors 20 are operable to measure the amount of deformation, the specific structure of the displacement sensors 20 is not limited to the example of the embodiment described above. For example, the displacement sensor 20 may be a capacitive sensor including a pair of electrodes and a dielectric layer interposed therebetween, configured to measure the amount of deformation by sensing changes in electrostatic capacity. Moreover, the displacement sensor 20 may be configured to sense the amount of deformation using, for example, light or a camera. The displacement sensor 20 may be made of a piezoelectric film in an exemplary aspect. It should be noted that examples of the displacement sensor 20 do not include sensors for measuring only electrical signals from muscles without measuring movements of the neck surface, such as an electromyography sensor.

In the embodiment described above, the cable 60 may be excluded. This means that the controller 100 may include a communication module to wirelessly transmit signals (e.g., Bluetooth®) to the external device 110.

In the embodiment described above, the condition under which setting of the reference value B0 is performed is not limited to the example of the embodiment described above. For example, the neck movement measuring device 10 may include a switch operable by a user; the controller 100 may start setting of the reference value B0 under the condition that the switch has been operated. That is, the switch can be a push-button, for example, that can activate the controller 100 to set the reference value B0. When the switch is a push-button, the controller 100 may start setting of the reference value B0 under the condition in which a user has pressed the push-button. In another example, the controller 100 may start setting of the reference value B0 after a predetermined specific period elapses since the power supply is turned on.

In the embodiment described above, the condition for setting the reference value B0 is not limited to the example of the embodiment described above. For example, the controller 100 may set the reference value B0 in accordance with the following five conditions. However, the following five conditions are merely examples, and setting the reference value B0 is not limited to these examples.

In a first example, under the condition in which the difference between two consecutive measured values of the displacement sensor 20 lies within a preset range of numerical values a preset number of times, the controller 100 sets the reference value B0.

In a second example, firstly, the controller 100 is configured to set a change amount between the first measured value A0 and a subsequent measured value as a reference change amount on each displacement sensor 20; under the condition in which the error of the change amount between two consecutive measured values to the reference change amount lies within a predetermined range of numerical values a preset number of times, the controller 100 sets the reference value B0.

In a third example, firstly, the controller 100 calculates the average value of the change amount between two consecutive measured values of ten consecutive measured values; under the condition in which the average value is within a preset range of numerical values, the controller 100 sets the reference value B0.

In a fourth example, firstly, the controller 100 calculates the average value of ten consecutive measured values on each displacement sensor 20; under the condition in which the ratio of the displacement sensors 20 with respect to the average value is within a preset range of numerical values, the controller 100 sets the reference value B0.

In a fifth example, firstly, the controller 100 calculates the average value of the change amount between two consecutive measured values of ten consecutive measured values; under the condition in which the ratio of the displacement sensors 20 with respect to the average value is within a preset range of numerical values, the controller 100 sets the reference value B0.

In the embodiment described above, the reference value B0 is not limited to the average value of measured values measured in the specific period. For example, the reference value B0 may be the median value, smallest value, greatest value, effective value, or moving average value of measured values measured in the specific period. Alternatively, the reference value B0 may be the average value or median value of measured values measured in the specific period minus the greatest and smallest values. Alternatively, the reference value B0 may be the average value or median value of measured values measured in the specific period minus the greatest, smallest, second greatest, and second smallest values. The reference value B0 may be set based on other indicators.

In the embodiment described above, the calculation of the sensed value B1 may be excluded. In this case, the controller 100 sets each threshold as a value for the reference value B0. In the embodiment described above, the sensed value B1 is not limited to a value obtained by dividing a measured value by the reference value B0. For example, the sensed value B1 may be the absolute value of the difference between a measured value and the reference value B0.

In the embodiment described above, after the controller 100 identifies masticatory movement, swallowing movement, or neck flexion movement of the user, the controller 100 may output the identification result by using, for example, light, sound, or vibration. In the embodiment described above, the neck movement measuring device 10 does not necessarily identify masticatory movement, swallowing movement, or neck flexion movement. For example, it is sufficient that the neck movement measuring device 10 be operable to detect subject's neck movement based on the difference between the reference value B0 and measured values.

In the embodiment described above, the first threshold X1, the second threshold X2, and the third threshold X3 are merely an example. Further, these thresholds are changeable based on, for example, sex or age of the subject.

In the embodiment described above, the controller 100 may identify masticatory movement, swallowing movement, or neck flexion movement of the user based on fluctuations in the sensed value B1 of the displacement sensors 20. For example, the fluctuations of the signals received from the displacement sensors 20 are converted in accordance with the fast Fourier transform (FFT) to calculate the amplitude at a particular frequency. When the amplitude at the particular frequency exceeds a particular value, corresponding movement is identified. The particular frequency may be determined, for example, by conducting a test to measure a typical frequency in masticatory movement, swallowing movement, and neck flexion movement.

In the embodiment described above, fluctuations in the sensed value B1 of the displacement sensors 20 may be subjected to an operation of removing signals of a particular frequency range, that is, band pass filtering. As the result of such an operation, subtle noises and signals based on non-target movements can be removed.

In an exemplary aspect, the controller 100 includes a central processing unit (CPU) and a read-only memory (ROM) to perform software processing for performing the algorithms and measurements described herein. In another aspect, the controller 100 may include a hardware circuit (for example, an application-specific integrated circuit (ASIC)) especially for performing hardware processing on at least a portion of the operations performed by software processing in the embodiment described above. Overall, the controller 100 may be configured in the following manners (a) to (c). (a) The controller 100 includes a processer for performing all the operations described above in accordance with a program and a program storage device for storing the program, such as a ROM. (b) The controller 100 includes a processer for performing a portion of the collection of operations described above in accordance with a program and a program storage device, and a hardware circuit especially for performing the rest of the operations. (c) The controller 100 includes a hardware circuit especially for performing the operations described above. The controller 100 may include a plurality of software processing devices including a processer and a program storage device and/or a plurality of dedicated hardware circuits.

The following describes some technical implementations based on the embodiment and modifications described above.

[1] A neck movement measuring device includes a displacement sensor attachable to the neck of a subject and a controller configured to output a measured value of the displacement sensor. The controller is configured to set a reference value based on a measured value of the displacement sensor and output a displacement amount relative to the reference value as a measurement result of the displacement sensor.

[2] In the neck movement measuring device according to [1], the controller is configured to start setting of the reference value after a specific period elapses since a power supply is turned on.

[3] The neck movement measuring device according to [1] further includes a switch operable by a user. The controller is configured to start setting of the reference value when the switch is operated.

[4] In the neck movement measuring device according to [1], the controller is configured to start setting of the reference value when a measured value of the displacement sensor indicates a deformation greater than or equal to a predetermined particular value.

[5] In the neck movement measuring device according to any one of [1] to [4], the reference value is the average value of measured values of the displacement sensor measured in a predetermined specific period.

[6] In the neck movement measuring device according to any one of [1] to [4], the reference value is the greatest value of measured values of the displacement sensor measured in a predetermined specific period. [7] In the neck movement measuring device according to any one of [1] to [4], the reference value is the smallest value of measured values of the displacement sensor measured in a predetermined specific period.

[8] In the neck movement measuring device according to any one of [1] to [4], when the difference between the greatest value and the smallest value of measured values of the displacement sensor measured in a predetermined specific period is a predetermined specific value or smaller, one value selected from the measured values measured by the displacement sensor in the specific period is set as the reference value.

[9] In the neck movement measuring device according to any one of [1] to [8], based on the displacement amount relative to the reference value, one or more movements selected from masticatory movement, swallowing movement, and neck flexion movement of a user are detected as neck movement of the user. P1 [10] In the neck movement measuring device according to [9], the controller is configured to, when the absolute value of the displacement amount relative to the reference value is greater than or equal to a predetermined first threshold and smaller than a predetermined second threshold that is greater than the first threshold, detect the masticatory movement as the neck movement. P1 [11] In the neck movement measuring device according to [10], the controller is configured to, when the absolute value is greater than or equal to the second threshold and smaller than a predetermined third threshold that is greater than the second threshold, detect the swallowing movement as the neck movement. P1 [12] In the neck movement measuring device according to [11], the controller is configured to, when the absolute value is greater than or equal to the third threshold, detect the neck flexion movement as the neck movement.

In general, it is noted that the embodiments described above are intended to facilitate the understanding of the present invention, and are not intended to limit or interpret the present invention. The present invention may be changed/modified without departing from the spirit thereof, and the present invention also includes equivalents thereof. In other words, the scope of the present invention is also inclusive of any embodiment subjected, as appropriate, by a person skilled in the art to a design change as long as specific features of the present invention are included. For example, elements provided in each embodiment and arrangement, material, condition, shape, size, and the like thereof are not limited to those illustrated and can be changed as appropriate. Moreover, elements provided in the embodiments can be combined as long as it is technically possible, and combinations thereof are also included in the scope of the present invention as long as specific features of the present invention are included.

What is claimed:

1. A neck movement measuring device comprising:
a sensor sheet;
a displacement sensor disposed on the sensor sheet and configured to be attached to a neck of a subject; and
a controller configured to:
set a reference value based on a measured value of the displacement sensor and after a set time period elapses since a power supply of the neck movement measuring device is turned on, and
output a displacement amount relative to the reference value as a measurement result of the displacement sensor,
wherein the displacement sensor comprises a plurality of displacement sensors that each are electrical conductors formed of a material with a resistance configured to change as each respective displacement sensor expands and contracts.

2. The neck movement measuring device according to claim 1, wherein the reference value is an average value of measured values of the displacement sensor measured during a predetermined time period.

3. The neck movement measuring device according to claim 1, wherein the reference value is a smallest value of measured values of the displacement sensor measured during a predetermined time period.

4. The neck movement measuring device according to claim 1, wherein, when a difference between a greatest value and a smallest value of measured values of the displacement sensor measured during a predetermined time period is a predetermined value or smaller, one value selected from the measured values measured by the displacement sensor in the predetermined time period is set as the reference value.

5. The neck movement measuring device according to claim 1, wherein the controller is configured to output the displacement amount, which indicates one of a masticatory movement, a swallowing movement, and a neck flexion movement as neck movement of the subject wearing the neck movement measuring device.

6. The neck movement measuring device according to claim 5, wherein the controller is configured to detect the swallowing movement as the neck movement when an absolute value of the displacement amount relative to the reference value is greater than or equal to a predetermined second threshold and smaller than a predetermined third threshold that is greater than the predetermined second threshold.

7. The neck movement measuring device according to claim 5, wherein the controller is configured to detect the neck flexion movement as the neck movement when an absolute value of the displacement amount relative to the reference value is greater than or equal to a predetermined threshold.

8. The neck movement measuring device according to claim 1, wherein each of the plurality of displacement sensors comprises an elongated sensing portion that extends in a direction parallel to a long axis of the sensor sheet, such that the respective elongated sensing portions are arranged parallel to each other.

9. The neck movement measuring device according to claim 8, wherein the sensor sheet has a plurality of slits arranged on both sides of each of the elongated sensing portions and extending in a direction perpendicular to the long axis.

10. The neck movement measuring device according to claim 1, wherein the controller comprises a memory and a central processing unit configured to execute software on the memory to set the reference value and output the displacement amount relative to the reference value as the measurement result of the displacement sensor.

11. The neck movement measuring device according to claim 1, further comprising a strip-shaped connector that connects the displacement sensor to the controller for providing the measured value of the displacement sensor to the controller.

12. A neck movement measuring device comprising:
a sensor sheet;
a displacement sensor disposed on the sensor sheet and configured to be attached to a neck of a subject; and
a controller configured to:
set a reference value based on a measured value of the displacement sensor, and
output a displacement amount relative to the reference value as a measurement result of the displacement sensor,
wherein the displacement sensor comprises a plurality of displacement sensors that each are electrical conductors formed of a material with a resistance configured to change as each respective displacement sensor expands and contracts, and
wherein the reference value is a greatest value of measured values of the displacement sensor measured during a predetermined time period.

13. A neck movement measuring device comprising:
a sensor sheet;

a displacement sensor disposed on the sensor sheet and configured to be attached to a neck of a subject; and a controller configured to:

set a reference value based on a measured value of the displacement sensor, and output a displacement amount relative to the reference value as a measurement result of the displacement sensor, wherein the displacement sensor comprises a plurality of displacement sensors that each are electrical conductors formed of a material with a resistance configured to change as each respective displacement sensor expands and contracts, wherein the controller is configured to output the displacement amount that indicates a masticatory movement as neck movement of the subject wearing the neck movement measuring device, and wherein the controller is configured to detect the masticatory movement as the neck movement when an absolute value of the displacement amount relative to the reference value is greater than or equal to a predetermined first threshold and smaller than a predetermined second threshold that is greater than the first threshold.

* * * * *